United States Patent [19]

Simchock

[11] Patent Number: Plant 7,130

[45] Date of Patent: Jan. 30, 1990

[54] IMPATIENS PLANT 'DAPPER DAN'

[76] Inventor: Daniel Simchock, 870 Broadway, Brentwood, N.J. 11717

[21] Appl. No.: 268,936

[22] Filed: Nov. 4, 1988

[51] Int. Cl.[4] ..... A01H 5/00
[52] U.S. Cl. ..... Plt./68
[58] Field of Search ..... Plt./68

[56] References Cited

U.S. PATENT DOCUMENTS

P.P. 39,186 6/1976 Hope et al. ..... Plt. 68

*Primary Examiner*—James R. Feyrer
*Attorney, Agent, or Firm*—Frank B. Robb

[57] ABSTRACT

An impatiens plant of the variety known as "Duet" in which the double deep red flowers are contrasted with foliage which is basically the usual green of impatiens leaves, but is provided with variegations in the form of yellowish white borders of varying widths extending around the edge of each of the leaves.

1 Drawing Sheet

BACKGROUND OF THE INVENTION

This invention relates to a new and distinct variety of Impatiens plant, which in many respects resembles its parents but is outstandingly different in that its foliage is variegated.

I have developed this plant in my greenhouse in Brentwood, N.Y. and have determined that it is definitely related to one of its parents as to the color of the flowers which are red and double as is the seed parent "Duet" and double but differing from its pollen parent which is also "Duet" but a pink white flower producer.

The variegation which is outstanding resides in the fact that the border of the leaves is basically a relatively thin portion which extends around the edge of the leaves and is of a yellowish white color, while the rest of the leaves in each case are the usual green of the parent and like that of other Impatiens plants with which I am familiar and which is characteristic.

As will be understood, the yellowish white border of the leaves which is the variegation which I have noted before is not necessarily uniform in width, but the light coloration is definitely defined, and does not extend throughout the surface of the leaves. It does thus provide a unique contrast to the overall appearance of the plant and presents a new and attractive contrast to the deep red of the flowers when the plant is displayed.

Portions of the darker green leaf shades with dark and washed dark green patterns are within the light green to white generally marginal, variegated hands.

While the floral display of my new impatiens is in fact similar to that of the parent "Duet" as to the double flowering and color, the variegation of the leaves in the yellowish white borders results in a markedly different impression from the red parent.

Flower buds are borne several to each stem and may occur in clusters at nodes. Buds of each cluster are of uneven maturity and normally only one open flower is presented from a cluster at a time. Flowers occur in moderate amounts and with at least one mature flower, per stem during the flowering season when the plant is used as an outdoor bedding plant. Growth habit is indeterminate indoors, but would normally be an annual in outdoor use as the plant is tender to frost.

I have caused my new variety to be asexually reproduced by stem cuttings at Brentwood, N.Y., and found that it retains the characteristics which make it distinctive, through successive generations.

The distinctive characteristics noted in my new variety which I have chosen to designate as "Dapper Dan", for commercial purposes, are disclosed in the drawing forming a part hereof, wherein the colors are as near the colors of the actual plant as is possible to reproduce by photographic processes used herein.

Color designations have been selected by comparison with the Munsell Color Fan, produced by Munsell Color Company.

Detailed description which assists in identifying my new plant are set forth in the appended material and summarized in the claim set forth hereinafter.

Parentage:

*Seedling.*—*"Duet"—Double red — Seed parent. "Duet"—Double pink-white — Pollen parent.*

Plant:

*Form.*—Short — full.

*Growth.*—Vigorous-compact. Even pattern — new spurs flower early — many side shoots off main shoot. Plant is sterile and thus seed formation is absent.

Foliage:

*Size.*—Medium.

*Quantity.*—Abundant — usually-to normal.

*Color.*—New foliage: Upper side-Inside-moderate olive green 5GY4/3. Variegation-border-brilliant green yellow 2.5GY9/8. Under side-Inside-Moderate olive green 5GY5/6. Variegation-border-brilliant green. Variegation same on new growth as in mature leaves. Yellow 2.5GY9/8. Old foliage: Upper side-Inside-Moderate olive green 5GY4/3. Variegation-border-whiter than 10Y9/9. Underside-Inside-Moderate olive green 5GY4/3. Variegation-border-whiter than 10Y9/9. The variegation of the leaves is provided by a border around each which varies in width, though usually thin with ragged inner edges, width often varying from leaf to leaf.

*Shape.*—Oval and oval pointed Texture — Upper side-smooth. Under side-smooth.

Flowers:

*Borne.*—Several to each stem in irregular clusters.

*Quantity.*—Moderate-outdoors and in greenhouse.

*Continuity.*—An annual-one season.

*Size.*—$1\frac{1}{2}$" to 2" through all conditions — all double with approximately the same number of petals. No seed formation noted.

*Color.*—Red 2.5R5/12.

Bud:

*Size.*—Medium size.

*Form.*—Medium.

*Color.*—Appears pink 7.5R9/3 to white.

*Peduncle.*—Medium. Stem color-Moderate yellow green 2.5GY5/5. Opens well and is not affected by adverse conditions.

Petals: Many petals under normal conditions. 20–25 red petals with 15–20 very small inner petals of whitish color under conditions observed. When fully open have white inside. Turn deep red as they get older.

*Texture.*—Thin.

*Form.*—Oval.

*Fragrance.*—None.

*Spurs.*—One per flower, inconspicuous.

I claim:

1. A mew and distinct variety of Impatiens plant characterized particularly as to novelty by the foliage wherein the borders of the leaves are of yellowish white coloration to thus provide variegation, the borders being of relatively thin width varying from leaf to leaf, thereby providing a unique contrast with the double deep red flowers which have the color of the deep red impatiens "Duet".

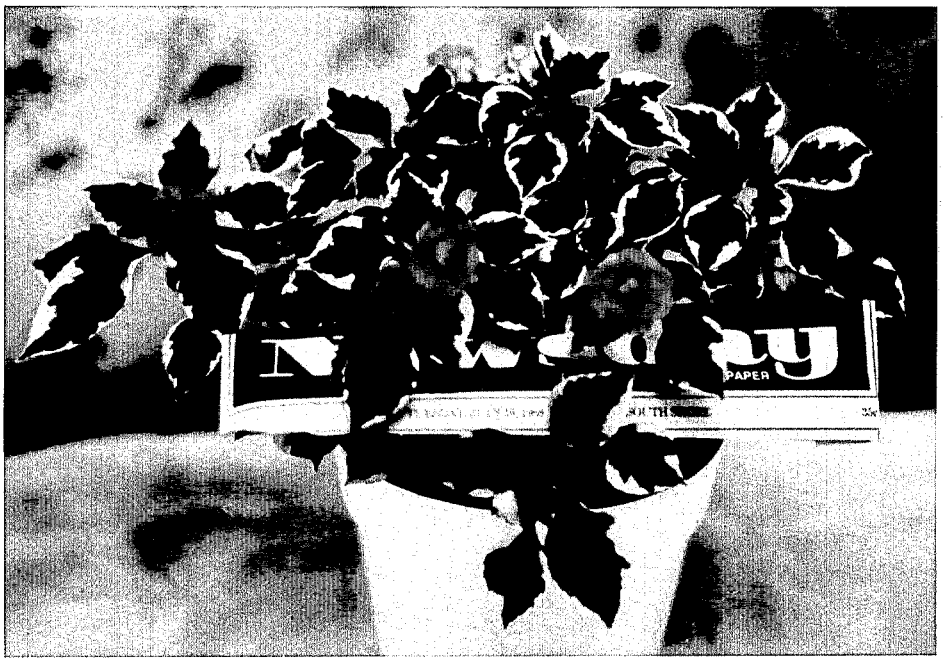

* * * * *